(12) United States Patent
van Oosterwijk et al.

(10) Patent No.: US 11,771,746 B2
(45) Date of Patent: Oct. 3, 2023

(54) METHOD TO REDUCE TICK POPULATION WITH A UNIVERSAL TICK ANTIGEN

(71) Applicant: US BIOLOGIC, INC, Memphis, TN (US)

(72) Inventors: Jolieke Gerdy van Oosterwijk, Memphis, TN (US); Douglas Steven Zatechka, Jr., Cordova, TN (US); Luciana Meirelles Richer, Memphis, TN (US)

(73) Assignee: US Biologic, Inc, Memphis, TN (US)

( * ) Notice: Subject to any disclaimer, the term of this patent is extended or adjusted under 35 U.S.C. 154(b) by 0 days.

(21) Appl. No.: 17/922,173

(22) PCT Filed: Jan. 10, 2022

(86) PCT No.: PCT/US2022/011772
§ 371 (c)(1),
(2) Date: Oct. 28, 2022

(87) PCT Pub. No.: WO2022/155084
PCT Pub. Date: Jul. 21, 2022

(65) Prior Publication Data
US 2023/0127041 A1    Apr. 27, 2023

Related U.S. Application Data

(60) Provisional application No. 63/138,315, filed on Jan. 15, 2021.

(51) Int. Cl.
*A61K 33/00*   (2006.01)
*A61K 39/00*   (2006.01)
*A61P 33/00*   (2006.01)
*A61P 33/14*   (2006.01)

(52) U.S. Cl.
CPC .......... *A61K 39/0003* (2013.01); *A61P 33/00* (2018.01); *A61K 2039/542* (2013.01); *A61K 2039/552* (2013.01); *A61P 33/14* (2018.01)

(58) Field of Classification Search
CPC .......... A61K 39/0003; A61K 2039/542; A61K 2039/552; A61P 33/00; A61P 33/14
See application file for complete search history.

(56) References Cited

U.S. PATENT DOCUMENTS

2014/0271702 A1* 9/2014 Guerrero ............... A61P 37/00
424/191.1
2016/0361396 A1* 12/2016 Scoles ............... C07K 14/43527
2017/0181975 A1 6/2017 Zatechka et al.

FOREIGN PATENT DOCUMENTS

CN   108642058 A   10/2018

OTHER PUBLICATIONS

Campbell et al. 2010 (Role of an aquaporin in the sheep tick *Ixodes ricinus*: Assessment as a potential control target; International Journal for Parasitology 40: 15-23). (Year: 2010).*
Embers et al. 2017 (Vaccination against Lyme disease: past, present and future; Frontiers in Cellular and Infection Microbiology; 3(6): 1-15). (Year: 2017).*
Barbour AG. Infection resistance and tolerance in *Peromyscus* spp., natural reservoirs of microbes that are virulent for humans. Semin Cell Dev Biol. Jan. 2017;61:115-122. doi: 10.1016/j.semcdb.2016.07.002. Epub Jul. 2, 2016.
Bhowmick B, Han Q. Understanding Tick Biology and Its Implications in Anti-tick and Transmission Blocking Vaccines Against Tick-Borne Pathogens. Front Vet Sci. Jun. 9, 2020;7:319. doi: 10.3389/fvets.2020.00319. Erratum in: Front Vet Sci. Aug. 31, 2020;7:575.
Campbell EM, Burdin M, Hoppler S, Bowman AS. Role of an aquaporin in the sheep tick *Ixodes ricinus*: assessment as a potential control target. Int J Parasitol. Jan. 2010;40(1):15-23. doi: 10.1016/j.ijpara.2009.06.010. Epub Jul. 25, 2009.
Campbell et al., Invertebrate aquaporins: a review. J Comp Physiol B. Nov. 2008;178(8):935-55. doi: 10.1007/s00360-008-0288-2. Epub Jul. 2, 2008.
Eisen RJ, Eisen L. The Blacklegged Tick, *Ixodes scapularis*: An Increasing Public Health Concern. Trends Parasitol. Apr. 2018;34(4):295-309. doi: 10.1016/j.pt.2017.12.006. Epub Jan. 11, 2018.
Finn RN, Cerdà J. Evolution and functional diversity of aquaporins. Biol Bull. Aug. 2015;229(1):6-23. doi: 10.1086/BBLv229n1p6.
Rodriquez, Kari. International Search Report and Written Opinion of the International Searching Authority. ISA Jul. 5, 2022. 1-86. PCT.
Šimo L, Kazimirova M, Richardson J, Bonnet SI. The Essential Role of Tick Salivary Glands and Saliva in Tick Feeding and Pathogen Transmission. Front Cell Infect Microbiol. Jun. 22, 2017;7:281. doi: 10.3389/fcimb.2017.00281.

* cited by examiner

*Primary Examiner* — Mary Maille Lyons
(74) *Attorney, Agent, or Firm* — VERITAY GROUP IP; Susan Fentress (57) ABSTRACT

Through the use of a universal anti-tick antigens, multiple tick-borne diseases that occur over a significant area can be targeted for eradication. The novel reservoir targeted anti-tick treatment is designed to reduce tick numbers and thereby blocking transmission of tick-borne diseases.

2 Claims, 3 Drawing Sheets
Specification includes a Sequence Listing.

FIG. 1

AQP_1 SEQ ID NO: 1

MQLFGNTVLAILTFEKASTDGLAACFWGWGLALTLGVLVAGGASGAHLNPAITVAVTTIGKFPWRKIVPYVLAQYIGAFIASVVLFITYRGALDNFDGGNRIVTGVNGTA

AQP_2 SEQ ID NO: 2

MASVGNPPFPFLRRFVTKNEAVKE

AQP_3 SEQ ID NO: 3

TGAGVSGGHVNPIVTTSFASVGKLPWRKVPHY

AQP_4 SEQ ID NO: 4

RQVTGEKGTAGIFATYP

AQP_5 SEQ ID NO: 5

TAGIFASYPKEF

AQP_6 SEQ ID NO: 6

NPARDLAPRVFTAM

AQP_7 SEQ ID NO: 7

DKAGNAGYGA

AQP_8 SEQ ID NO: 8

GAGMNVARSFGPAVMSGMF

AQP_9 SEQ ID NO: 9

DALSQIDANLTTVYGI NATAPVFSCFPAPGVST

AQP_10 SEQ ID NO: 10

GWGGEVFSFRDYN

SEQUENCE LISTING

```
<160> NUMBER OF SEQ ID NOS: 10

<210> SEQ ID NO 1
<211> LENGTH: 110
<212> TYPE: PRT
<213> ORGANISM: Artificial Sequence
<220> FEATURE:
<223> OTHER INFORMATION: Synthetic

<400> SEQUENCE: 1

Met Gln Leu Phe Gly Asn Thr Val Leu Ala Ile Leu Thr Phe Glu Lys
1               5                   10                  15

Ala Ser Thr Asp Gly Leu Ala Ala Cys Phe Trp Gly Trp Gly Leu Ala
            20                  25                  30

Leu Thr Leu Gly Val Leu Val Ala Gly Gly Ala Ser Gly Ala His Leu
        35                  40                  45
```

```
Asn Pro Ala Ile Thr Val Ala Val Thr Thr Ile Gly Lys Phe Pro Trp
 50                  55                  60
Arg Lys Ile Val Pro Tyr Val Leu Ala Gln Tyr Ile Gly Ala Phe Ile
 65                  70                  75                  80
Ala Ser Val Val Leu Phe Ile Thr Tyr Arg Gly Ala Leu Asp Asn Phe
                 85                  90                  95
Asp Gly Gly Asn Arg Ile Val Thr Val Asn Gly Thr Ala
                100                 105                 110

<210> SEQ ID NO 2
<211> LENGTH: 24
<212> TYPE: PRT
<213> ORGANISM: Artificial Sequence
<220> FEATURE:
<223> OTHER INFORMATION: Synthetic

<400> SEQUENCE: 2

Met Ala Ser Val Gly Asn Pro Pro Phe Pro Phe Leu Arg Arg Phe Val
 1               5                  10                  15
Thr Lys Asn Glu Ala Val Lys Glu
                 20

<210> SEQ ID NO 3
<211> LENGTH: 32
<212> TYPE: PRT
<213> ORGANISM: Artificial Sequence
<220> FEATURE:
<223> OTHER INFORMATION: Synthetic

<400> SEQUENCE: 3

Thr Gly Ala Gly Val Ser Gly Gly His Val Asn Pro Ile Val Thr Thr
 1               5                  10                  15
Ser Phe Ala Ser Val Gly Lys Leu Pro Trp Arg Lys Val Pro His Tyr
                 20                  25                  30

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Arg Gln Val Thr Gly Glu Lys Gly Thr Ala Gly Ile Phe Ala Thr Tyr
 1               5                  10                  15
Pro

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Thr Ala Gly Ile Phe Ala Ser Tyr Pro Lys Glu Phe
 1               5                  10

<210> SEQ ID NO 6
<211> LENGTH: 14
<212> TYPE: PRT
<213> ORGANISM: Artificial Sequence
<220> FEATURE:
```

```
<223> OTHER INFORMATION: Synthetic

<400> SEQUENCE: 6

Asn Pro Ala Arg Asp Leu Ala Pro Arg Val Phe Thr Ala Met
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Asp Lys Ala Gly Asn Ala Gly Tyr Gly Ala
1               5                   10

<210> SEQ ID NO 8
<211> LENGTH: 19
<212> TYPE: PRT
<213> ORGANISM: Artificial Sequence
<220> FEATURE:
<223> OTHER INFORMATION: Synthetic

<400> SEQUENCE: 8

Gly Ala Gly Met Asn Val Ala Arg Ser Phe Gly Pro Ala Val Met Ser
1               5                   10                  15

Gly Met Phe

<210> SEQ ID NO 9
<211> LENGTH: 33
<212> TYPE: PRT
<213> ORGANISM: Artificial Sequence
<220> FEATURE:
<223> OTHER INFORMATION: Synthetic

<400> SEQUENCE: 9

Asp Ala Leu Ser Gln Ile Asp Ala Asn Leu Thr Thr Val Tyr Gly Ile
1               5                   10                  15

Asn Ala Thr Ala Pro Val Phe Ser Cys Phe Pro Ala Pro Gly Val Ser
            20                  25                  30

Thr

<210> SEQ ID NO 10
<211> LENGTH: 13
<212> TYPE: PRT
<213> ORGANISM: Artificial Sequence
<220> FEATURE:
<223> OTHER INFORMATION: Synthetic

<400> SEQUENCE: 10

Gly Trp Gly Gly Glu Val Phe Ser Phe Arg Asp Tyr Asn
1               5                   10
```

METHOD TO REDUCE TICK POPULATION WITH A UNIVERSAL TICK ANTIGEN

BACKGROUND OF THE INVENTION

Incorporation by reference of the material in the ASCII text file:

Applicant hereby specifically incorporates by reference the file PATENTIN_ST25, created on 01/04/2021 and –3.23 kb insize.

FIELD OF INVENTION

The subject matter disclosed herein provides a method to disrupt tick homeostasis by providing tick aquaporin antigens to the pathogen host.

BACKGROUND

Ticks and tick-borne diseases are significant and increasing threats to public health in the United States. Contributing to increased cases of tick-borne disease are emergence of novel tick-borne pathogens, expanding geographic ranges of multiple tick species, and increased populations of ticks.

In North America, two main tick species, with small rodent reservoirs, are responsible for transmission of a variety of diseases to humans. As each of those ticks infest small rodents, such as *Peromyscus leucopus* (white footed mouse), during early life cycle stages (larvae and nymphs), and these rodents are primary disease reservoirs), these mice provide a unique opportunity to stop multiple disease threats before it reaches the human population. For example, *Borrelia burgdorferi*, causative agent of Lyme borreliosis and transmitted by *Ixodes scapularis*, is the most commonly occurring tick-borne infection in the United States with approximately 30,000 cases annually reported to the Centers for Disease Control and Prevention. Based upon laboratory testing records, annual incidence of Lyme disease in the United States is estimated to be greater than 300,000 cases. The U.S. costs of this disease could range between $50B and $100B.

In addition to *Borrelia burgdorferi*, *Ixodes scapularis* is the primary competent vector for *Anaplasma phagocytophilum*, *Babesia microti*, *Borrelia miyamotoi*, *Borrelia mayonii*, *Ehrlichia murise auclairensis*, and Powassan virus. With the exception of *Ehrlichia muris eauclairensis*, whose reservoir host is not determined, *Peromyscusleucopus* is an established vertebrate reservoir for these human pathogens. *Ixodes scapularis* transmitted pathogens are an increasing burden of disease individually and as co-infections, particularly with *Borrelia burgdorferi*. Contributing to the disease increase is the significant geographic range expansion of *Ixodes scapularis* in the Eastern and Midwestern United States during the past two decades. By 2016, *Ixodes scapularis* was established in 44.7 percent of all United States counties (Eisen 2016).

Prevention of tick-borne disease relies upon personal protective behaviors to prevent tick bites, including repellents, tick checks, and environmental suppression of tick populations by use of chemical acaricides. Despite these measures, the incidence of tick transmitted diseases continues to grow. Furthermore, there are currently no licensed human treatments in the United States for tick-borne pathogens.

Aquaporins (AQPs) are molecularly well characterized integral membrane channels essential for water transport (Finn 2015) in vertebrate and invertebrate species (Campbell 2008). Tick aquaporins play a critical role in maintaining water homeostasis in the tick during feeding on a host, such as *Peromyscus leucopus*, and are therefore crucial for tick survival (Campbell 2010). The tick aquaporin has high sequence similarity across tick species and is distributed throughout the entire length of the gut. Aquaporin is a tick molecule essential for physiological integrity salivary gland function. Novel methods are urgently needed to reduce encounters of humans with infected tick vectors and to reduce pathogen transmission.

SUMMARY OF THE INVENTION

Through the use of a universal anti-tick antigens, multiple tick-borne diseases that occur over a significant area of North America can be targeted for eradication. The novel reservoir targeted anti-tick treatment is designed to reduce tick numbers and thereby blocking transmission of tick-borne diseases. The inventive subject matter includes a method to reduce tick population in the wild comprising administering to mice at least one aquaporin peptide selected from the group consisting of SEQ ID NO1-SEQID NO 10, wherein the method further includes the step of administering an expression vector harboring a nucleic acid molecule encoding the at least one aquaporin peptide. The inventive subject matter includes formulating the expression vector harboring a nucleic acid molecule for delivery in the wild as a microencapsulated bead.

More specifically, the inventive subject matter includes: a method of controlling zoonotic infectious diseases by vaccinating a subject in need thereof comprising orally administering to the subject a composition for oral delivery of a bait foodstuff, said bait foodstuff comprising: i) a bait substrate having a surface; ii) an effective amount of at least one antigenic agent layered over said substrate, wherein said at least one antigenic agent is stabilized within a stabilizer under conditions facilitating anhydrobiosis, said stabilizer selected from at least one of the group consisting of a hydrocolloid polymer and a plasticizing sugar, complexed in solution with a phosphate-buffered saline liquid carrier; and iii) a calcium salt cross-linking agent to facilitate encapsulation of said antigenic agent within said stabilizer on said surface of said substrate; wherein said antigenic agent is a bacterial vehicle, said bacterial vehicle defined by a recombinant bacteria engineered to express at least one antigen, wherein the antigen is a synthetic or semi-synthetic aquaporin which can be selected from the group consisting of: SEQ ID NO 1-SEQ ID NO 10.

BRIEF DESCRIPTION OF THE DRAWINGS

The novel features of the invention are set forth with particularity in the claims. Features and advantages of the present invention are referred to in the following detailed description, and the accompanying drawings of which:

DETAILED DESCRIPTION OF THE INVENTION

The details of one or more embodiments of the presently disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as commonly understood by one of ordinary skill in the art to which the presently disclosed subject matter belongs. Although any methods, devices, and materials similar or equivalent to those described herein can be used in the practice or testing of the presently disclosed subject matter, representative methods, devices, and materials are now described. Following long-standing patent law convention, the terms "a", "an", and "the" refer to "one or more" when used in this application, including the claims. Thus, for example, reference to "a cell" includes a plurality of such cells, and so forth. All references to singular characteristics or limitations of the present disclosure shall include the corresponding plural characteristic(s) or limitation(s) and vice versa, unless otherwise specified or clearly implied to the contrary by the context in which the reference is made. All combinations of method or process steps as used herein can be performed in any order, unless otherwise specified or clearly implied to the contrary by the context in which the referenced combination is made. The methods and compositions of the present disclosure, including components thereof, can comprise, consist of, or consist essentially of the essential elements and limitations of the embodiments described herein, as well as any additional or optional components or limitations described herein or otherwise useful. Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method. As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed.

Through the use of a universal anti-tick antigens, multiple tick-borne diseases that occur over a significant area of North America can be targeted for eradication. The novel reservoir targeted anti-tick treatment is designed to reduce tick numbers and thereby blocking transmission of tick-borne diseases. Aquaporins are molecularly well characterized integral membrane channels essential for water transport (Finn 2015) in vertebrate and invertebrate species (Campbell 2008). Tick aquaporins play a critical role in maintaining water homeostasis in the tick during feeding on a host, such as *Peromyscusleucopus*, and are therefore crucial for tick survival (Campbell 2010). The tick aquaporin has high sequence similarity across tick species and is distributed throughout the entire length of the gut (Simo 2017).

Figure 1:
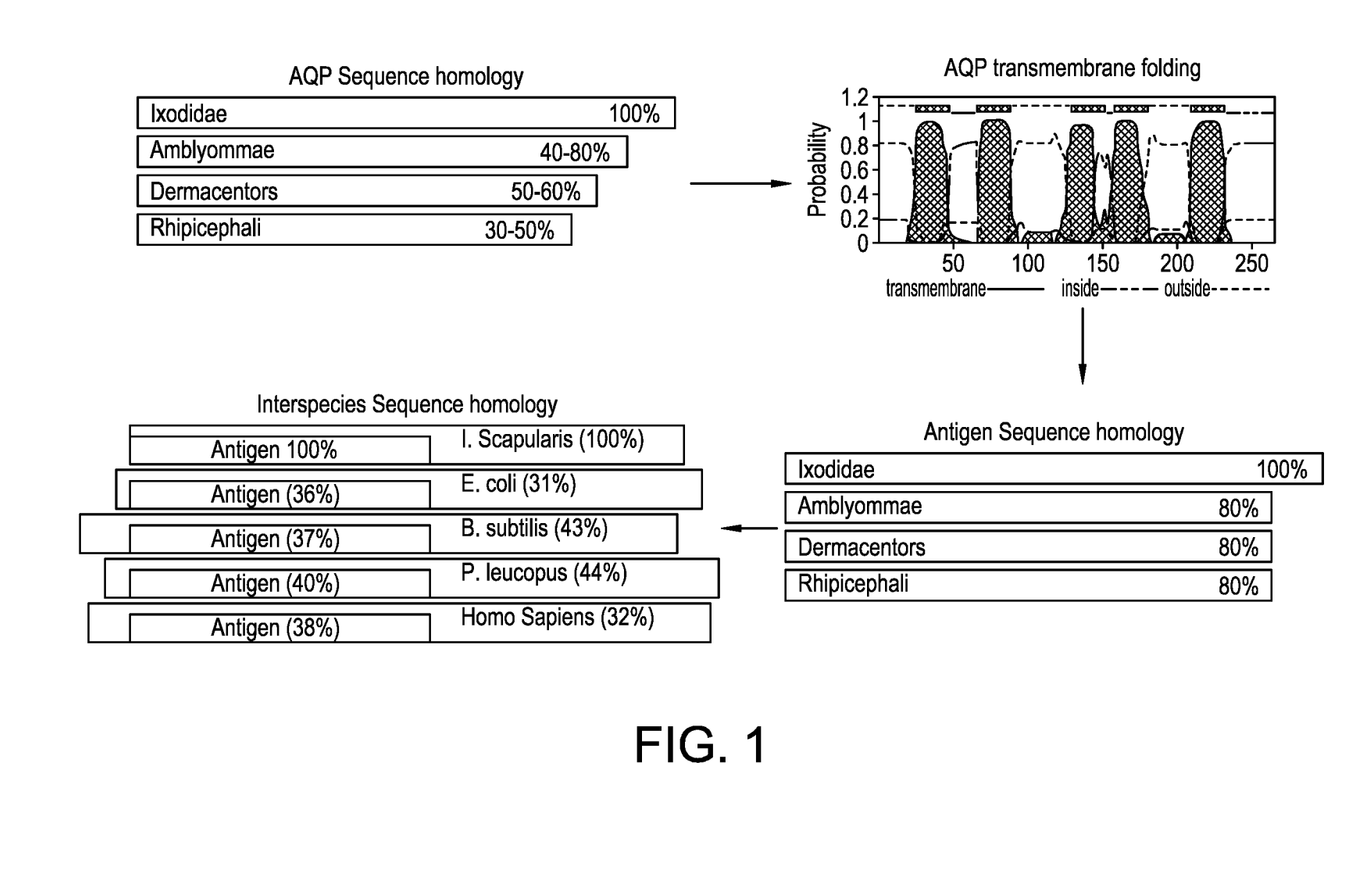
FIG. 1 shows genetic analysis of the Ixodid AQP sequence was compared to the AQP sequences reported for other tick species. Transmembrane folding analysis was used to identify extracellular domains, which were most likely to elicit a functional immune response. Subsequent homology modeling of transmembrane domains led to isolation of a highly conserved sequence within the AQP protein.
Figure 2:
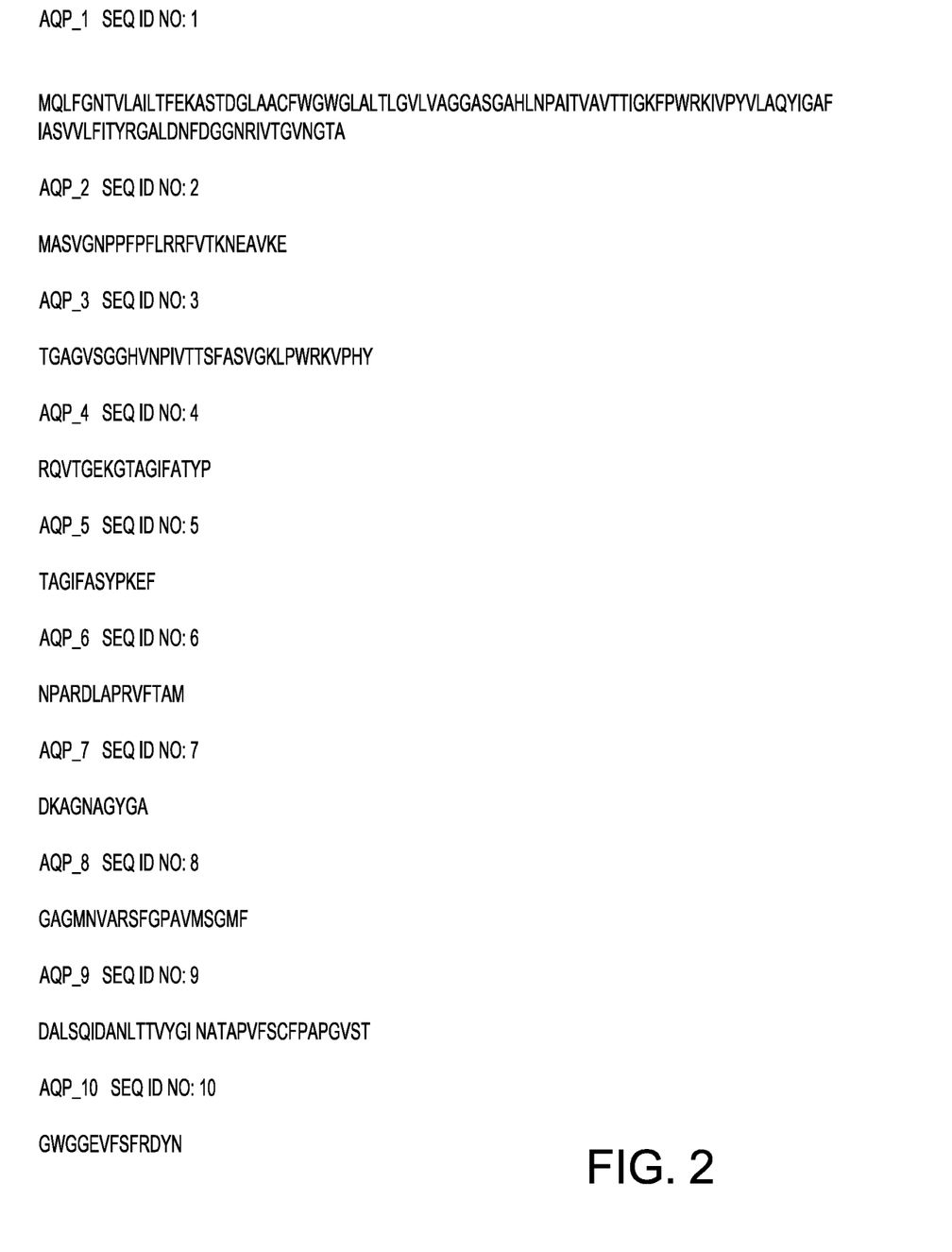
FIG. 2 shows the amino acid sequence of various Anti-tick Antigens.

Now referring to FIGS. 1-2, the Ixodid aquaporin sequence was compared to those of other tick species, and areas of high conservation were identified. See e.g. Campbell 2008 (Simo 2017)

The aquaporin protein sequence was analyzed for transmembrane folding, and extracellular epitopes were compared to those highly conserved sequences to yield a group of peptides set out as SEQ ID NO 1-SEQ ID NO 10. As AQPs occur in species other than ticks, the sequences were aligned with the expression vector, the target host species (*Peromyscusleucopus*) and humans, to address safety concerns, and minimize cross-reaction. The selected antigen was prepared for expression in a bacterial vehicle using sequence optimization. Importantly, the designed AQP antigen has high sequence homology across ticks (>80%) but low sequence similarity with the expression vehicle, target species, or humans (<40%, FIG. 3). For the purpose of this invention, the sequence "identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

Expression Vectors. One of ordinary skill in the art will appreciate that any of a number of expression vectors are suitable for introducing a nucleic acid sequence to target species.

Nucleic Acid Molecules. The expression vector of the invention harbors nucleic acid molecules. Ideally, the nucleic acid molecules encode an aquaporin peptide. One of ordinary skill in the art appreciate that any transcription factor can be modified or truncated and retain activity. As such, therapeutic fragments (i.e., those fragments having biological activity sufficient to activate transcription) also are suitable for incorporation into the expression vector.

Nucleic acid molecules encoding the aquaporin peptide can be present as part of an expression cassette, a particular base sequence that possess functions which facilitate subcloning and recovery of a nucleic acid molecule or expression of the nucleic acid molecule.

An isolated nucleic acid is a nucleic acid the structure of which is not identical to that of any naturally occurring nucleic acid. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

The term recombinant nucleic acids refer to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Where a recombinant nucleic acid is intended for expression, cloning, or replication of a particular sequence, DNA constructs prepared for introduction into a prokaryotic or eukaryotic host will typically include a replication system (i.e., vector) recognized by the host, including the intended DNA fragment encoding a desired polypeptide, and can also include transcription and translational initiation regulatory sequences operably linked to the polypeptide-encoding segment. Expression systems (expression vectors) can include, for example, an origin of replication or autonomously replicating sequence and expression control sequences, a promoter, an enhancer and necessary processing information sites, such as ribosome-binding sites, RNA splice sites, polyadenylation sites, transcriptional terminator sequences, and mRNA stabilizing sequences. Signal peptides can also be included where appropriate from secreted polypeptides of the same or related species, which allow the protein to cross and/or lodge in cell membranes, cell wall, or be secreted from the cell.

Selectable markers useful in practicing the methodologies of the invention disclosed herein can be positive selectable markers. Typically, positive selection refers to the case in which a genetically altered cell can survive in the presence of a toxic substance only if the recombinant polynucleotide of interest is present within the cell. Negative selectable markers and screenable markers are also well known in the art and are contemplated by the present invention. One of skill in the art will recognize that any relevant markers available can be utilized in practicing the inventions disclosed herein.

Screening and molecular analysis of recombinant strains of the present invention can be performed utilizing nucleic acid hybridization techniques. Hybridization procedures are useful for identifying polynucleotides, such as those modified using the techniques described herein, with sufficient identity to the subject regulatory sequences to be useful as taught herein. See, e.g., Sambrook et al. (1989) vide infra or Ausubel et al. (1995) Current Protocols in Molecular Biology, John Wiley & Sons, N.Y., N.Y., for further guidance on hybridization conditions. Additionally, screening, and molecular analysis of genetically altered strains, as well as creation of desired isolated nucleic acids can be performed using Polymerase Chain Reaction (PCR).

Hybridization-based screening of genetically altered strains typically utilizes homologous nucleic acid probes with identity to a target nucleic acid to be detected. The extent of identity between a probe and a target nucleic acid can be varied according to the particular application. Identity can be 50%-100%. In some instances, such identity is greater than 80%, greater than 85%, greater than 90%, or greater than 95%. The degree of identity or identity needed for any intended use of the sequence(s) is readily identified by one of skill in the art. As used herein percent sequence identity of two nucleic acids is determined using the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used.

An AQP sequence was cloned into a high copy *Bacillus subtilis* expression vector, which encodes the endogenous *Bacillus* antitoxin EndoB, under the control of a xylose-inducible promotor. The vectored-amp-AQP was expanded using *Escherichia coli* cells and purified using plasmid purification. Sequences were confirmed using Sanger sequencing and the vectored-amp-AQP plasmids were digested using EcoRI and ScaI restriction enzymes (Thermo Fisher), to excise the ampicillin resistance cassette. Bands of correct length were gel purified and digestion and gel purification were repeated to ensure complete digestion and removal of all *Escherichia coli* DNA. The purified linearized plasmids were subsequently re-ligated using Rapid DNA Ligation (Thermo Fisher). In some embodiments of the presently disclosed subject matter, a composition for oral delivery of an aquaporin peptide effector molecules is provided. The composition includes a substrate, an effective amount of at least one aquaporin peptide effector molecules coated or layered on a substrate, and a cross-linking agent to facilitate the encapsulation of the aquaporin peptide effector molecules in the stabilizer on the surface of the substrate. In some embodiments, the at least one bioactive agent is stabilized in a stabilizer selected from a group consisting of a hydrocolloid polymer further made of a plasticizing sugar to include sucrose. Still further, in some embodiments, a method of preparing a composition for oral delivery of a bioactive agent is provided. The method includes the steps of uniquely passaging and culturing the at least one bioactive agent; osmotically preconditioning the at least one bioactive agent; stabilizing at least one bioactive agent in a stabilizer; coating the stabilized at least one bioactive agent on to a substrate; applying a cross-linking agent; cross-linking to facilitate gelation or encapsulation of bioactive agent; and drying under forced air at an ambient temperature. In some embodiments, the temperature is in a range of between about −50° C. to about −80° C. In some embodiments, the temperature is in a range of between about 0.03 mBar to about 0.0005 mBar. In some embodiments, the temperature is in a range of between about 20° C. to about 35° C. In some embodiments, a fan drives the ambient temperatures. In some embodiments, the methods further include a step of coating with a confectionary glaze layer on the exterior surface for moisture barrier or flavored attractant. In some embodiments, the method further includes a step of coating with a shellac layer on the exterior surface for moisture barrier.

Current methods for generating calcium-alginate encapsulated biological materials require the generation of hydrogel or calcium-alginate beads. Bead-encapsulated biological materials are generated by the pressurized dispensing of sodium alginate into a volume of calcium salt, a process employing specific encapsulation equipment (an encapsulator) (Mazzitelli et al., *J. Biomat. Appl.* 23:123, 2008). Calcium-alginate beads generated by an encapsulator can be harvested and dried for downstream application. The bead format does not render itself beneficial or efficient for the uniform application In some embodiments, the bioactive agent is osmotically pre-conditioned for anhydrobiosis and stabilization. As used herein, the term "osmotically preconditioned" refers to the use of specific solutes employed to physically stabilize and protect membranes and proteins in intact bacteria prior to drying to desiccation. Non-limiting osmotic preconditioners include plasticizing agents such as sugars, to include sucrose and/or trehalose, or hydroxyectoine. As used herein, the term "anhydrobiosis" refers to the physical state of biological tolerance to desiccation. In some embodiments, the bioactive agent is stabilized in a stabilizer. Stabilization refers to the means of promoting and maintaining the biological activity of the bioactive agent, wherein the whole-cell carrier is structurally maintained for effective presentation of protein as an immunogen. Non-limiting stabilizers incorporate the use of hydrocolloids. As used herein, the term "hydrocolloid" will refer to any material of the colloid family of hydrophilic polymers dispersed in aqueous solution. Hydrocolloids present, in some embodiments, as small particles of about 1 to about 1000 nm in diameter and serve to encapsulate and stabilize biological material. A hydrocolloid of the present disclosure may include, but is not limited to, agar, alginate, carrageenan, chitosan, gelatin, and/or gum. Suitable hydrocolloids may include one or more natural and synthetic polymers, which form colloidal solutions in aqueous systems. Preferable hydrocolloids include polysaccharides, such as alginic acid, sodium alginate, and calcium alginate. Suitable hydrocolloids include polyvinyl pyrrolidones; starch; cellulose and cellulose derivatives, such as ethyl cellulose, methyl cellulose, hydroxypropylmethyl cellulose (HPMC), hydroxypropyl cellulose (HPC), and carboxymethylcellulose (CMC); polyethylene glycol (PEG); or mixtures thereof. As used herein, hydrocolloids are employed as liquid carriers for the at least one bioactive agent for feasible application as a liquid coating around the substrate. In some embodiments, the liquid carrier also serves to include application of visualization tracer formulations. As used herein, visualization tracer formulations include the divalent salts of barium, to include barium sulfate. As used herein, preparation of barium sulfate in the context of the liquid carrier stabilized by layered encapsulation over the substrate provide a means by which substrate administration formulation can be visualized via X-ray for gastro-intestinal (GI) dissolution. As used herein, GI dissolution further provides added assurance of the stabilization of the agent for presentation of the protein payload to the gut-associate lymphoid tissues (GALT). In some embodiments, the liquid carrier also serves to include application of active pharmaceutical ingredients (APIs) as further measure of GALT dissolution and systemic metabolism of the liquid carrier stabilized by layered encapsulation over the substrate. As used herein, APIs can include, but are not limited to, the use of Ivermectin. As used herein, GALT-level dissolution of the API-liquid carrier stabilized by layered encapsulation can be measured via serological assay of Ivermectin by high-pressure liquid chromatography (HPLC). In some embodiments, certain hydrocolloid polymers, such as sodium alginate, may be cross-linked in the presence of a calcium salt. Cross-linking in the presence of a divalent cation such as calcium refers to the capacity to structurally link the polymeric bonds of the hydrocolloid polymer, sodium alginate, to calcium to generate a polymer of calcium alginate cross-linked bonds; calcium ions replace the sodium ions in the alginate polymer yielding what is termed polymerization. Polymerization via cross-linking facilitates the stabilized encapsulation of the aquaporin peptide effector molecules as used in the presently disclosed subject matter. In some embodiments, the cross-linking agent is a calcium salt. Examples of cross-linking agent include, but are not limited to, calcium lactate, calcium butyrate, calcium chloride, calcium sulfate, calcium carbonate, calcium acetate, or calcium ascorbate. As used in the presently disclosed subject matter, the cross-linking agent facilitates polymerization of the stabilizer. As presented herein the composition of the presently disclosed subject, the composition relates to a composition made of a substrate and an effective amount of at least one biologically active agent stabilized by layered encapsulation over the substrate. As used herein, the term substrate relates to a substance of solid support, suitable for oral consumption, upon which or around which (as a shell or coating) may be applied the osmotically preconditioned stabilized at least one bioactive agent. In some embodiments, the substrate has a mean diameter of from about 100 μm to about 5 cm. In some embodiments, the composition may be of a size of about no more than 10 cm to accommodate consumption by target animal species. In some embodiments of the presently disclosed subject matter, examples of the substrate include, but is not limited to pellet, a chewable, a bead and a powder. In some embodiments, the substrate is a plant-based or earthen-based substance. In some embodiments, the earthen-based substance includes but is not limited to soil or water. In some embodiments, the substrate further includes, but is not limited to, a plant and/or forage material to include grass, herbaceous legumes, tree legumes, silage, or crop residues to include grains such as corn or soybean stover, or other earthen-based substance, such as soil, compost, or addition directly to water. In certain embodiments, the substrate is edible, and appropriate to be fed to animals in a composition. In some embodiments, the substrate can include: a dried pellet or kibble, such as a particle generated by compressing original material, which may be broken up upon mastication into particulate material; and/or a chewable particle, soft and pliable in nature, such that it is not readily broken up or reduced to particulate matter upon mastication but may be readily dissolved; and/or a composition that may bypass the ruminant digestive processes such as a ruminant undegradable protein (RUP) substrate; micro-crystalline cellulose beads or other substrate for employment in the generation and application of aquaporin peptide effector molecules. in powdered formulation for administration via nasal inhalation, or to be administered directly to water as a hydrocolloidal suspension as an oral administration via drinking; a plant; a food-source, such as a food source that is available in the wild; and/or another earthen substance, soil or other onto which the aquaporin peptide effector molecule is then dried for stability, or water into which may be applied the aquaporin peptide effector molecules for consumption by drinking. In some embodiments, the composition further includes a coating on the exterior surface of the composition. In some embodiments, the coating is an enteric coating. In some embodiments, the coating on the exterior surface of the substrate is sequentially applied in layers as a top-dressing and is an enteric coating once cross-linked. In some embodiments, the substrate is in an amount of about 85% to about 99% w/w of the composition. In some embodiments, the stabilizer is in an amount of about 1% to about 15% w/w of the composition. In some embodiments, the effective amount of the bioactive agent is an immunogenically effective amount with the minimal immunizing dosage (MID) of about $5 \times 10^3$ CFU to about $5 \times 10^{11}$ CFU. In some embodiments, cross-linking agent is in an amount of about 0.5% to about 7.5% w/w of the composition. Further, in some embodiments, the coating is in an amount of about 1.5% to about 22.5% w/w of the composition.

The following examples are offered to illustrate, but not to limit the invention.

EXAMPLES

Example 1

Figure 3:
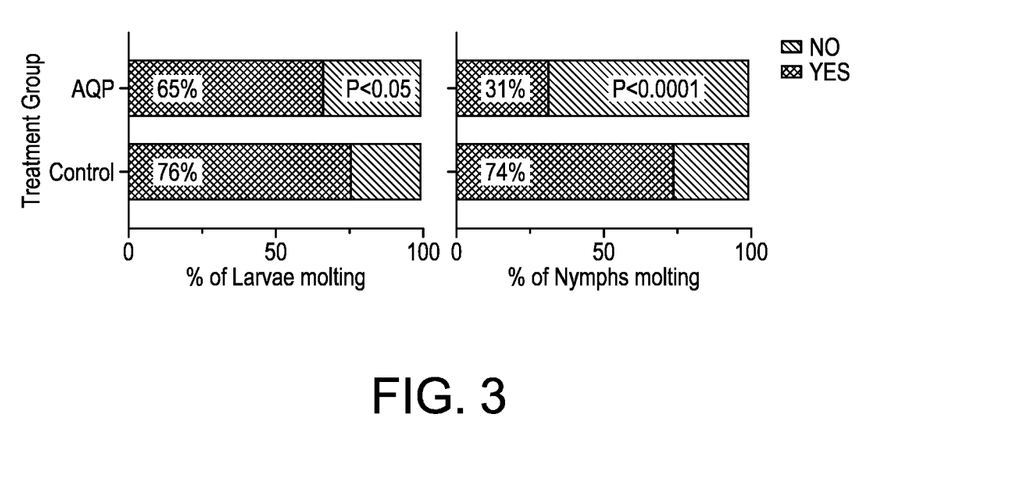
FIG. 3 shows molting of *Ixodes scapularis* ticks after feeding on AQP vaccinated mice. Larvae (left) and nymphs (right) were placed on AQP vaccinated and control mice. Ticks were allowed to feed until detached and detached ticks were placed in the laboratory under molting conditions. A reduction in the percentage of larvae successfully molting into nymphs was observed (p<0.05, two-tailed Fisher's exact test). A significant reduction in the percentage of nymphs successfully molting into adults was observed (p<0.0001, two-tailed Fisher's exact test

To test the safety and efficacy of the AQP treatment, pilot trials were conducted in laboratory mice (C3H). AQP treatment was provided to the mice on pellets, for oral delivery. Three trials with five mice were performed, where mice were given the opportunity to feed on AQP treatment coated pellets. Mice were on a prime-boost schedule, with four weeks in between. Three weeks after the boost, mice were challenged with five nymphal *Ixodes scapularis* and 50 larval *Ixodes scapularis*. Detached *Ixodes scapularis* ticks were collected and allowed to molt in the laboratory. A reduction in larvae molting into nymphs was observed ($p<0.05$, two-tailed Fisher's exact test), and a significant reduction in nymphs molting to adult *I. scapularis* ticks was observed ($p<0.0001$, two-tailed Fisher's exact test) (FIG. 3).

While the invention has been described with reference to details of the illustrated embodiments, these details are not intended to limit the scope of the invention as defined in the appended claims. The embodiment of the invention in which exclusive property or privilege is claimed is defined as follows:

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment. While the terms used herein are believed to be well understood by one of ordinary skill in the art, definitions are set forth herein to facilitate explanation of the presently disclosed subject matter.

INCORPORATION BY REFERENCE

All publications, patents and patent applications mentioned in this specification are herein incorporated by reference to the same extent as if each individual publication, patent or patent application was specifically and individually indicated to be incorporated by reference.

Barbour A G. Infection resistance and tolerance in *Peromyscus* spp., natural reservoirs of microbes that are virulent for humans. *Semin Cell Dev Biol.* 2017; 61:115-122. DOI:10.1016/j.semcdb.2016.07.002.

Campbell E M, Ball A, Hoppler S, Bowman A S. Invertebrate aquaporins: a review. *J Comp Physiol B.* 2008; 178(8):935-55. DOI: 10.1007/s00360-008-0288-2. Epub 2008 Jul. 2.

Campbell E M, Burdin M, Happier S, Bowman A S. Role of an aquaporin in the sheep tick *Ixodesricinus*: assessment as a potential control target. *Int J Parasitol.* 2010; 40:15-23, DOI:10.1016/j.ijpara.2009.06.010.

Eisen R J, Eisen L, Beard C B. County-scale distribution of *Ixodesscapularis* and *Ixodespacificus*(Acari: Ixodidae) in the continental United States. *J. Med Entomol.*2016; 53:349-386. DOI:10.1093/jme/tjv237.

Finn R N, Cedra J. Evolution and functional diversity of aquaporins. *Biol Bull.* 2015; 229(1):6-23. DOI:0.1086/BBLv229n1p 6.

Simo L, Kazimirova M, Richardson J, Bonnet S I. The essential role of tick salivary glands and saliva in tick feeding and pathogen transmission. Front Cell Infect Microbiol; 2017. DOI:10.3389/fcimb.2017.00281.

---

What is claimed is:

1. A method to reduce tick population comprising administering to mice an expression vector harboring a nucleic acid molecule encoding a peptide of SEQ ID NO. 1.

2. The method of claim 1, wherein the expression vector harboring a nucleic acid molecule is formulated for delivery as a microencapsulated bead.

* * * * *